United States Patent [19]

Golias

[11] 4,391,689
[45] Jul. 5, 1983

[54] AUTOMATED ELECTROPHORESIS AND STAINING APPARATUS AND METHOD

[75] Inventor: Tipton L. Golias, Beaumont, Tex.

[73] Assignee: Helena Laboratories Corporation, Beaumont, Tex.

[21] Appl. No.: 273,162

[22] Filed: Jun. 12, 1981

[51] Int. Cl.³ .............................................. B01D 57/02
[52] U.S. Cl. ........................... 204/180 G; 204/299 R
[58] Field of Search ........................ 204/180 G, 299 R

[56] References Cited

U.S. PATENT DOCUMENTS 3,290,240 12/1966 Neren .............................. 204/299 R
3,494,846 2/1970 Arguembourg ................. 204/299 R

*Primary Examiner*—John F. Niebling
*Attorney, Agent, or Firm*—Cullen, Sloman, Cantor, Grauer, Scott & Rutherford

[57] ABSTRACT

An automated electrophoresis and staining apparatus provides within a cabinet a housing with front and rear walls having opposed pairs of longitudinally spaced notches in their upper edges. Each pair of notches is adapted to successively receive and support a plate holder rack having a horizontal open frame supporting an upright electrophoresis plate onto which has been applied a sample for electrophoretic fractionization. An electrophoresis chamber and a series of vats are mounted within the housing and arranged in a row, the vats adapted to contain liquid stain and a series of plate processing solutions. The pairs of notches are in registry with the centerline of the chamber and each vat. The plate is nested within the chamber within an electrophoretic circuit for a predetermined period. A power operated lift and transfer assembly within the cabinet is adapted to lift, transfer and lower the plate holder rack and plate from the chamber and progressively into each of the underlying vats and a drying chamber for a predetermined period in a linear stepping motion, maintaining the plate in an upright position at all times. The method of electrophoresis which includes supporting in an upright position, a non-conductive plate having on one surface a buffer moistened electrophoresis media to which has been applied a sample selected from a group consisting of serum proteins, lipoproteins, hemoglobins and isoenzymes and enclosing the plate within a chamber. Applying an electrical potential to the plate ends within an electrical power circuit for a predetermined period at a preselected voltage, the specimen fractionating and migrating laterally through portions of the media. Elevating the plate, laterally translating the plate and lowering the plate while in an upright position, immersing it within a stain solution for a predetermined interval, and successively translating the plate to and into a series of vats containing processing solutions, and into a drying chamber.

30 Claims, 10 Drawing Figures

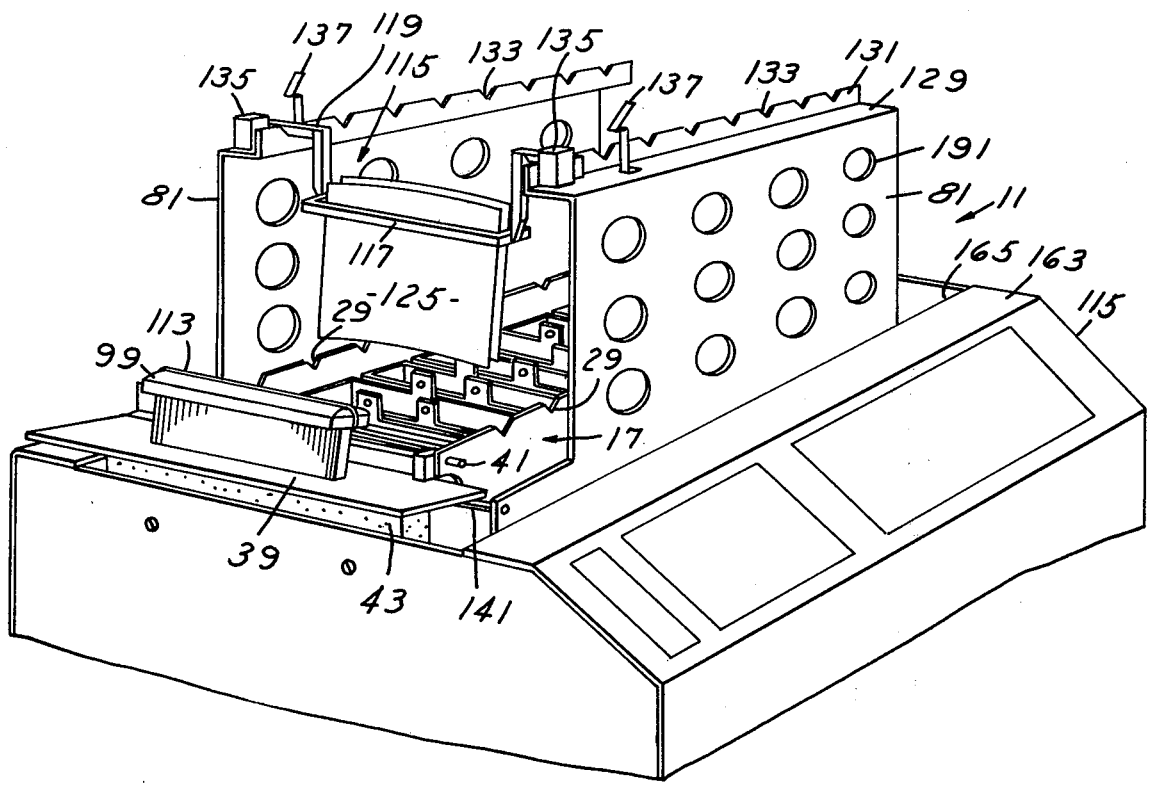
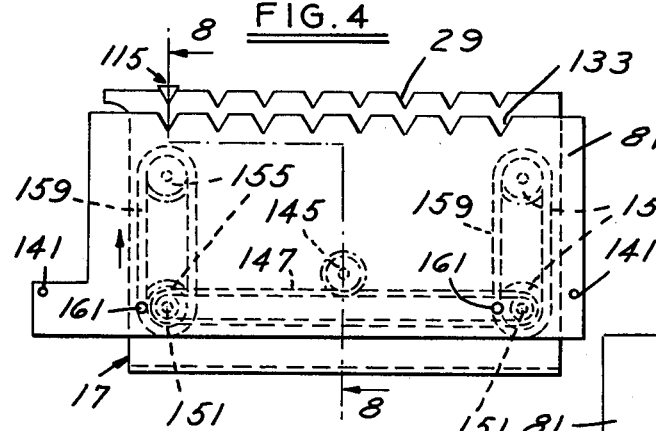
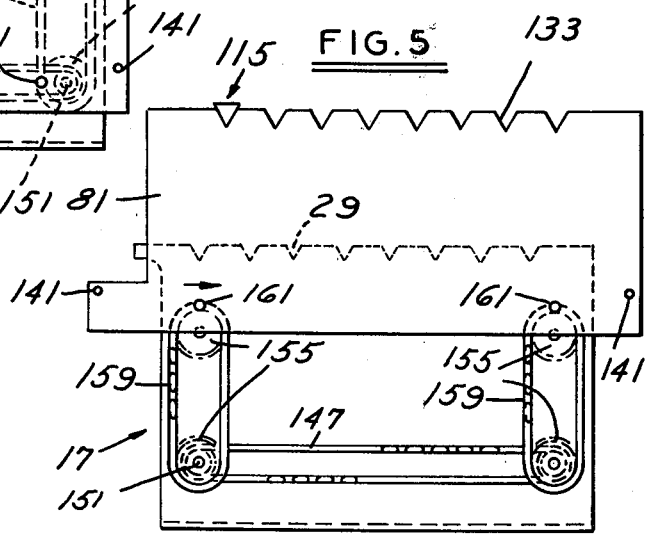

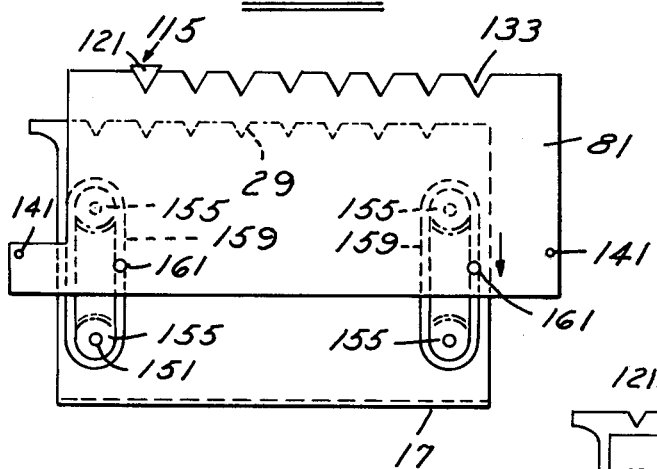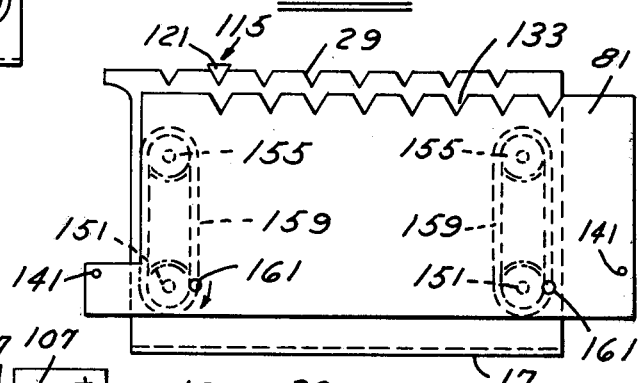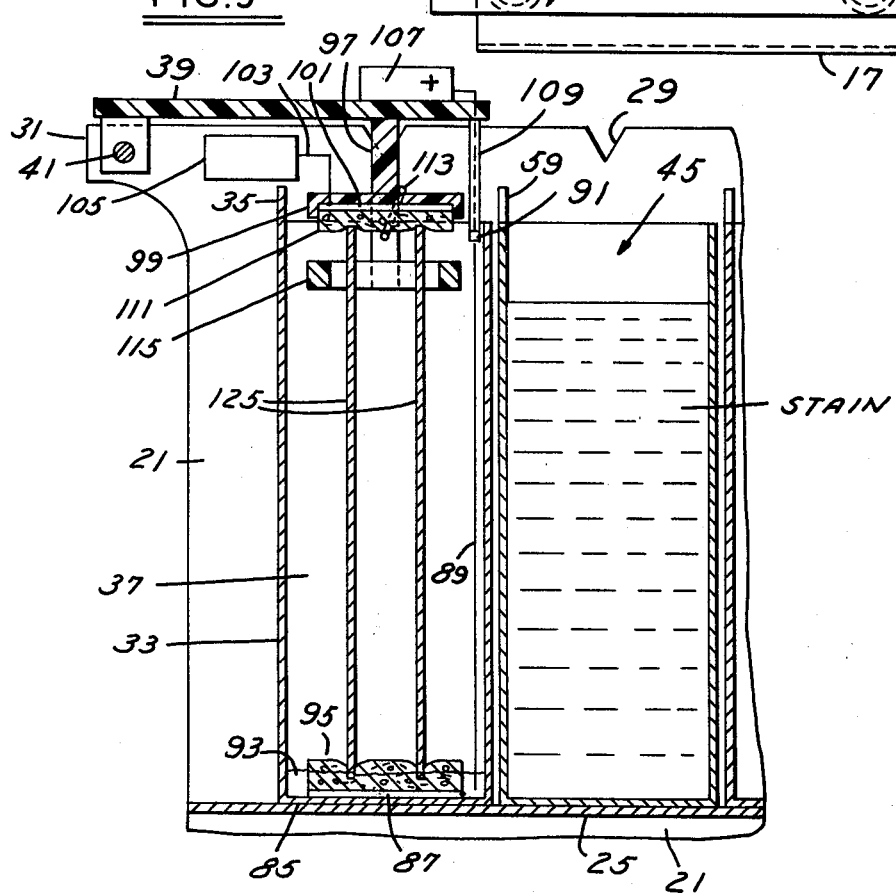

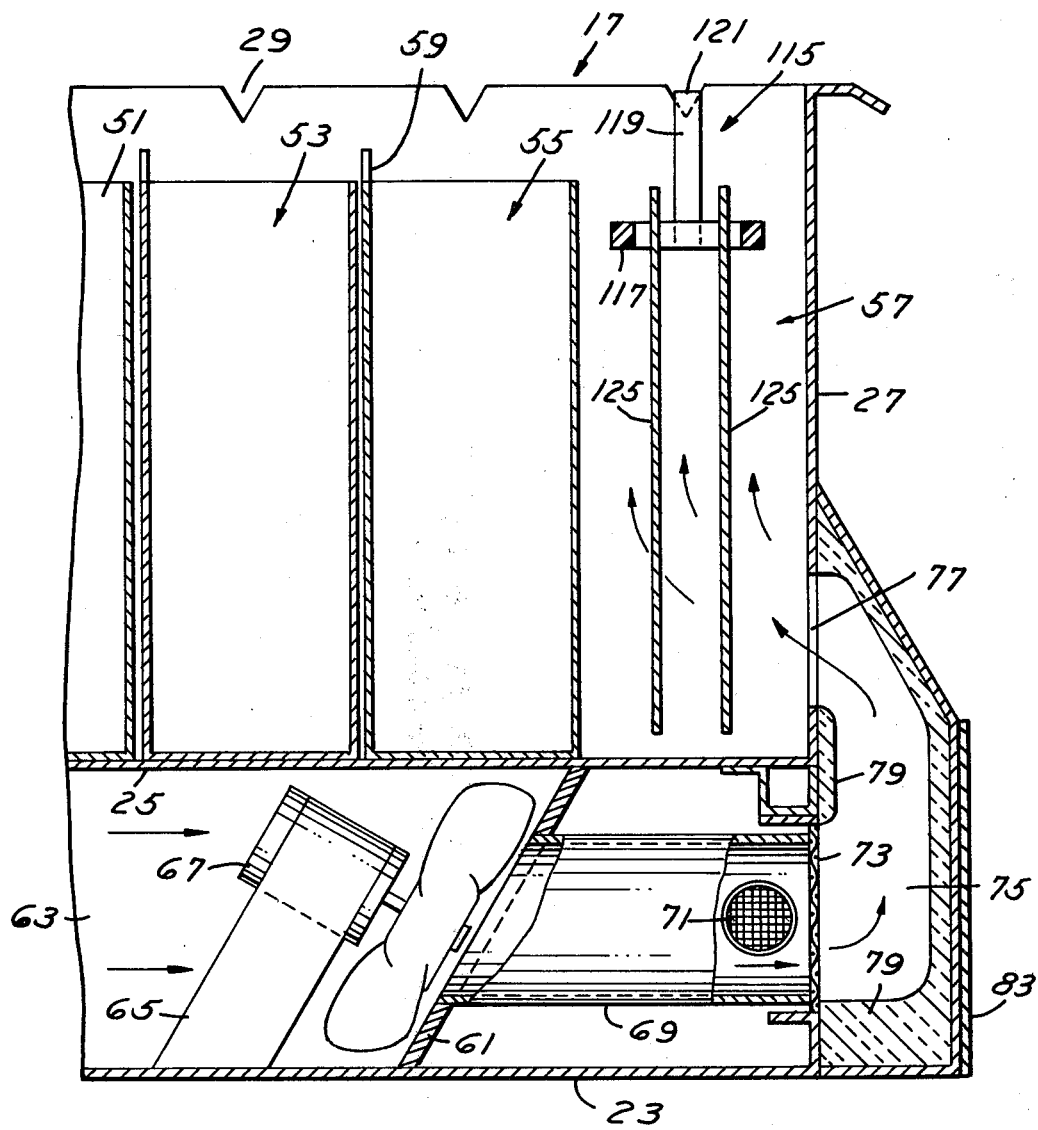

AUTOMATED ELECTROPHORESIS AND STAINING APPARATUS AND METHOD

BACKGROUND OF THE INVENTION

PRIOR ART

In the diagnosing of ailments of persons and animals, it is known that much information can be provided by an analysis of certain biological fluids such as serum proteins, lipoproteins, hemoglobins and isoenzymes. Electrophoresis as a method of separating the respective ingredients of said fluids, for a microscopic analysis or employing optical densitometry is known and shown or disclosed in one or more of the following patents:

| UNITED STATES PRIOR ART | | |
|---|---|---|
| 3,607,695 | Schneider | 9/21/71 |
| 3,759,773 | Dwyer et al | 9/18/73 |
| 3,808,118 | Golias | 4/30/74 |
| 3,873,433 | Seidel, et al | 3/25/75 |
| 3,884,764 | Goodhue | 5/20/75 |
| 3,907,642 | William Richmond | 9/23/75 |
| 3,907,645 | William Richmond | 9/23/75 |
| 3,912,610 | Kingdon Lou | 10/14/75 |
| BRITISH PRIOR ART | | |
| 1,060,874 | Stanton | (1966) |
| 1,211,008 | Elevitch | (1967) |
| 1,212,844 | Stanton | (1967) |
| 1,385,319 | William Richmond | (1972) |
| 1,385,320 | William Richmond | (1972) |
| 1,466,040 | Behringwerke Aktiengesellschaft | (1975) |

In the basic method of electrophoresis, charged molecules of fluids are separated under the influence of an electrical field wherein the sample of solution to be examined is mounted upon a support medium having a buffer moistened porous surface. Since the various components move at different rates, there is migration thereof laterally through the support media, the sample may be separated into its respective elements. The subsequent staining of the fractions prepare the plate when dried for examination by optical densitometry or other methods.

SUMMARY OF THE INVENTION

An important feature of the present invention is to provide an automated electrophoresis and staining apparatus wherein an electrophoresis plate has applied thereto a sample for electrophoretic fractionization and supported in an upright position by a transfer frame so that the plate may be projected downwardly into an electrophoresis chamber for a predetermined period within an electrophoretic circuit.

A further feature is the provision in conjunction with the electrophoresis chamber of a plurality of solution containing vats arranged in a line within a housing such that the plate may be transferred to a vat containing a stain solution and successively to other processing solutions at all times maintaining the plate in an upright position.

A further feature provides opposed pairs of longitudinally spaced notches upon the upper edges of the housing front and rear walls adapted to successively receive and support a plate holder rack which has a horizontal frame adapted for supporting one or a plurality of electrophoresis plates or media in registry with the underlined chamber, vats and a drying chamber within said cabinet.

A further feature is the provision of an electrophoresis chamber having a hinged cover within which the plate holder rack and the plates are supported which includes an electrical circuit with conductors and the use of conductive buffer moistened sponges in registry with the top and bottom edges of the plates for completing an electrical circuit through the electrophoresis plates. A further feature incorporates a safety mechanism within the electrophoresis chamber by which high voltage electrical potential may not be applied until the cover is closed over the chamber and the electrical circuit completed.

A further feature includes a power operated lift and transfer assembly within the cabinet, arranged outwardly of the front and rear walls of the housing, adapted to progressively lift, transfer and lower the plate holder rack and the plates from the chamber and progressively into each of the underlying vats for a predetermined period successively in a linear stepping motion with the plates maintained at all times in an upright position.

A further feature incorporates within the housing, an upright plate drying chamber together with a means for providing heated air upwardly through the drying chamber for application to the plates suspended therein.

A further feature is the specific electrophoresis chamber wherein an electrophoretic circuit is provided upon the interior thereof protectively enclosed by a pivoted cover and after a predetermined period, a power operated lift and transfer assembly on elevation automatically opens the cover so as not to block the upward movement of the rack and plates suspended therefrom.

A further feature is to provide an automated electrophoresis and staining apparatus which includes the process of electrophoresis and necessary sample staining in a continuous operation.

A further feature of the present invention is a control panel by which the timing of the electrophoresis process may be predetermined depending upon the sample being fractionated wherein the voltage applied may be modified for a particular electrophoresis depending upon the nature of this sample tested. The control panel has associated therewith, a program selector by which the interval of immersion within the respective vats and drying chamber may be preset according to a predetermined program or may be manually controlled.

A further feature includes a method of electrophoresis wherein there is included the step of supporting in an upright position a nonconductive plate having on one surface a buffer moistened electrophoresis media to which has been applied a sample selected from the group consisting of serum proteins, lipoproteins, hemoglobins and isoenzymes. Enclosing of the plate within an electrophoresis chamber after applying an electrical potential to the plate ends within an electrical power circuit for a predetermined period at a predetermined voltage, wherein the specimen fractionates and migrates laterally through portions of the media and after staining, is available for analysis by optical densitometry or other methods.

These and other objects will be seen from the following specification and claims in conjunction with the appended drawings.

THE DRAWINGS

FIG. 3, is a fragmentary end perspective view of the electrophoresis and staining apparatus with the lift and transfer assembly in an elevated position and with the cover of the electrophoresis chamber open.

FIG. 4, is a fragmentary schematic side elevational view of the lift and transfer assembly at the beginning of its rise relaive to the housing.

FIG. 5, is a similar view of the lift mechanism at the top of its rise and translated one half of the distance to transfer of the plate holder rack from one position to the next adjacent position.

FIG. 6 is a similar view of the transfer assembly at a point of its straight downward movement relative to the housing.

FIG. 7 is a similar view with the transfer assembly moved down towards its lowermost position, prior to retraction to the position shown in FIG. 4.

FIG. 9 is a fragmentary vertical section taken in the direction of arrows 9—9 of FIG. 8.

FIG. 10 is a fragmentary vertical section taken in the direction of arrows 10—10 of FIG. 1, and on an increased scale illustrating the drying chamber and the source of heated air thereto.

It will be understood that the above drawings illustrate merely a preferred embodiment of the invention including the apparatus and the method employed, and that other embodiments are contemplated within the scope of the claims hereafter set forth.

DETAILED DESCRIPTION OF AN EMBODIMENT OF THE INVENTION

Figure 1:
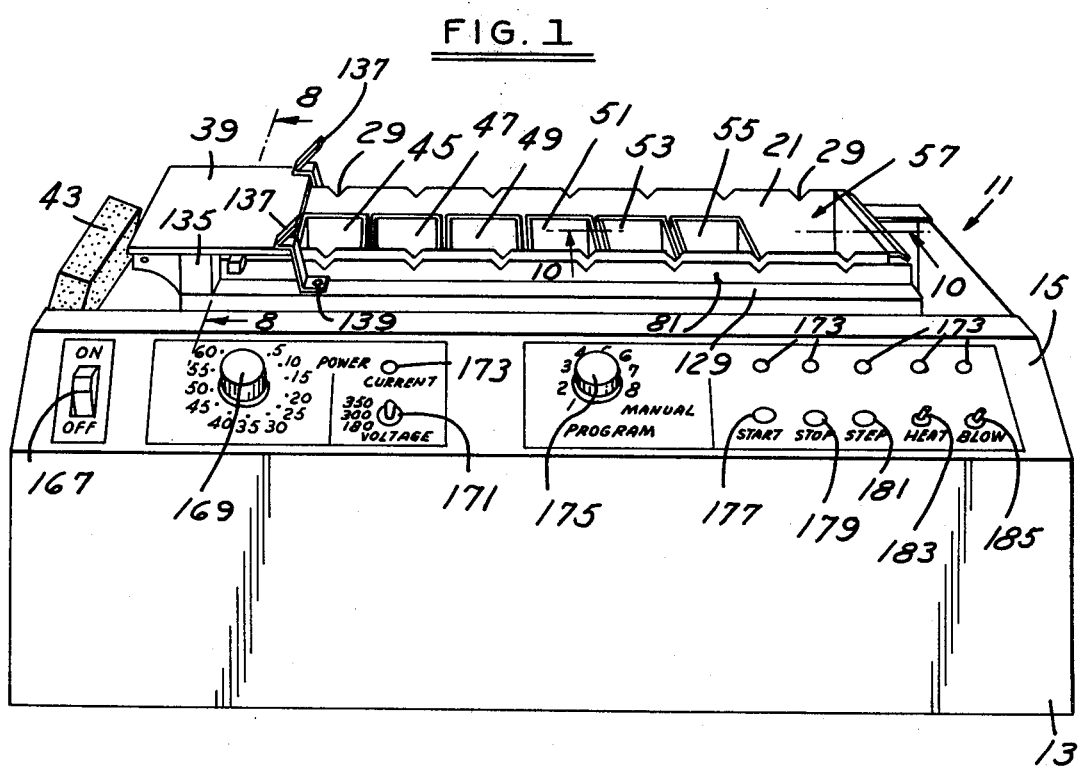
FIG. 1, is a front perspective view of the present automated electrophoresis and staining apparatus.

The present automated electrophoresis and staining apparatus, sometimes referred to as a system, it generally indicated at 11 in FIGS. 1 and 3 and includes an elongated cabinet 13 having a control panel 15. Positioned within the cabinet is an elongated housing 17 having front wall 19, rear wall 21 bottom wall 23 and spaced above the bottom wall, the overlying horizontal platform 25, as in FIG. 8. The housing also includes upright end wall 27 in FIG. 10.

Upon and along the top edges of the front and rear walls 19 and 21 are transversely aligned longitudinally spaced pairs of V notches 29, though they could be of another shape, such as U-shape. At the end of the housing opposite the end wall 27, at the upper ends of the front and rear walls, are a pair of opposed rearwardly extending bosses 31, FIG. 9, which are spanned by the hinge rod 41, which pivotally mounts the cover 39 for electrophoresis chamber 37.

Mounted upon the platform 25 within said housing and underlying cover 39 is a plastic container 33, which provides the electrophoresis chamber 37 and includes at its upper end, aperture lift boss 35. The boss 35 facilitates assembly and removal of container 33 from the housing, for its positioning upon platform 25. During the period of electrophoresis within chamber 37, cover 39 remains in the closed position shown in FIG. 9 for a predetermined interval and thereafter is automatically moved to the open position shown in FIG. 3 bearing against the transverse lid stop 43 upon cabinet 13.

A series of vats, preferably constructed of an inert material, such as plastic are mounted upon platform 25, side by side and arranged in a row and aligned with chamber 37. These vats are adapted to contain respectively a liquid stain as in the first vat 45, first rinse solution in vat 47, FIG. 1, second rinse solution in vat 49, third rinse solution in vat 51, a fixative solution in vat 53 and a final rinse solution in vat 55.

Upright drying chamber 57 is provided within housing 17 upon platform 25 and is arranged between the last vat 55 and the housing end wall 27, FIGS. 1 and 10. Each of the vats 45, 47, 49, 51, 53 and 55 have at the top thereof on one side, the upright aperture lift boss 59, FIG. 9, to facilitate proper positioning thereof within the housing upon platform 25 and removal therefrom from changing the solutions contained therein.

As shown in FIG. 10, within the housing 17 betweend the platform 25 and bottom wall 23, there is an elongated air chamber 63 communicating with atmosphere at one end and within which is positioned upon support 65 an electric fan 67. In the illustrative embodiment and for improved efficiency in the delivery of drying air, the fan is inclined at an acute angle corresponding to the angle of apertured baffle 61 within air chamber 63. Elongated air tunnel 69 extends from baffle 61 and has an outlet adjacent the end of the housing including an apertured grate 73 through which forced air passes into the warm air passage 75, which is insulated at 79 and has an air outlet 77 adjacent the lower end of drying chamber 57.

A cylindrical electrical heating element 71 is disposed within and transversely of the air tunnel 69 and when energized, provides for the passage of heated air through the air tunnel passage 75 and air outlet 77 into the lower end of the drying chamber 57 for upward movement as shown by the arrows in FIG. 10.

Figure 8:
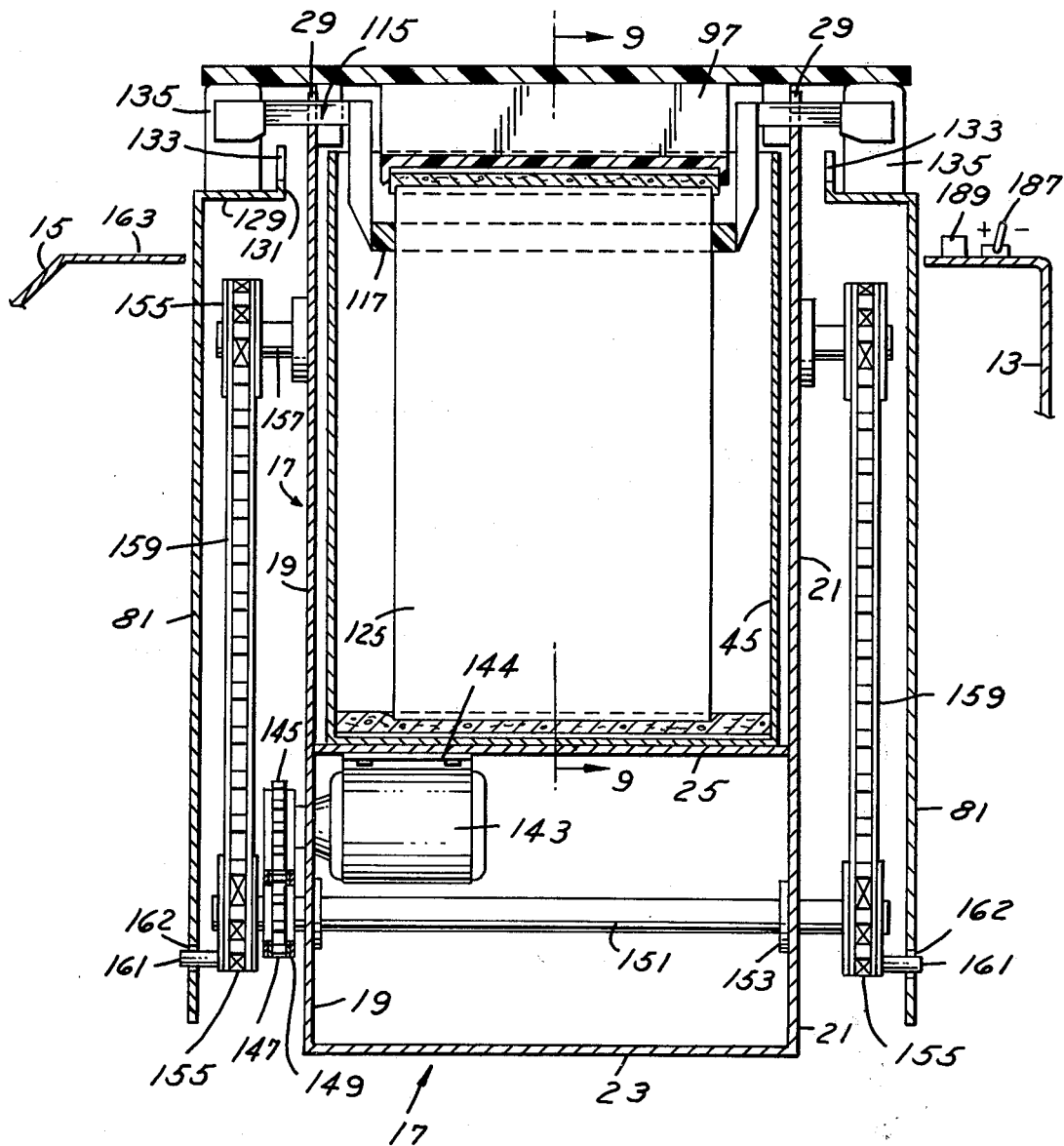
FIG. 8 is a fragmentary vertical section taken in the direction of arrows 8—8 of FIG. 1 and on an increased scale.

There is employed a power operated lift and transfer assembly within the cabinet 13 and arranged outwardly of the housing 17, which in the illustrative embodiment includes a pair of upright parallel spaced lift and transfer plates 81, FIG. 8. These are interconnected at their opposite ends as by the connector rods 141, FIG. 4, and further at their one ends by the transverse lift connector plate 83, shown in its lowermost position, FIG. 10. Said plate will be elevated with respect to the drying chamber 57 when the transfer mechanism has been elevated such as to the position shown in FIG. 5.

ELECTROPHORESIS CHAMBER

The electrophoresis chamber 37 within the container 33 as in FIG. 9 has a bottom wall 85 over which is positioned a platinum wire electrode 87. Lead 89 extends from said electrode and terminates at the upper end of the chamber 37 in contact 91. A quantity of buffer solution 93 is provided within the bottom of chamber 37, and a buffer moistened elongated sponge wick 95 partly immersed in the solution. One example of a buffer solution provided is:

Barbital 1.84 gm, Sodium Barbital 10.30 gm dissolved in one liter of water.

Upon the undersurface of the cover 39 is a transverse elongated flange 97 mounting a downwardly facing elongated sponge holder 99 within which is nested an elongated platinum electrode 101 terminating in the lead 103 which extends to the normally open tilt switch 105, depending from the cover 39. An additional normally open tilt switch 107 is schematically shown upon the cover 39, and would normally depend from the interior thereof, and is connected to a suitable power source in an electrical circuit and includes a depending contact 109. The contact 109 at its lower end is in registry with the first electrode contact 91, when the cover 39 is in the closed position shown in FIG. 9.

An additional buffer moistened sponge 111 of generally rectangular shape is positioned within the sponge holder 99 bears against conductor 101 and is retained therein by one or two elongated rubber bands 113 which extend lengthwise around the sponge holder 99 and around the under surface portions of sponge 111.

Figure 2:
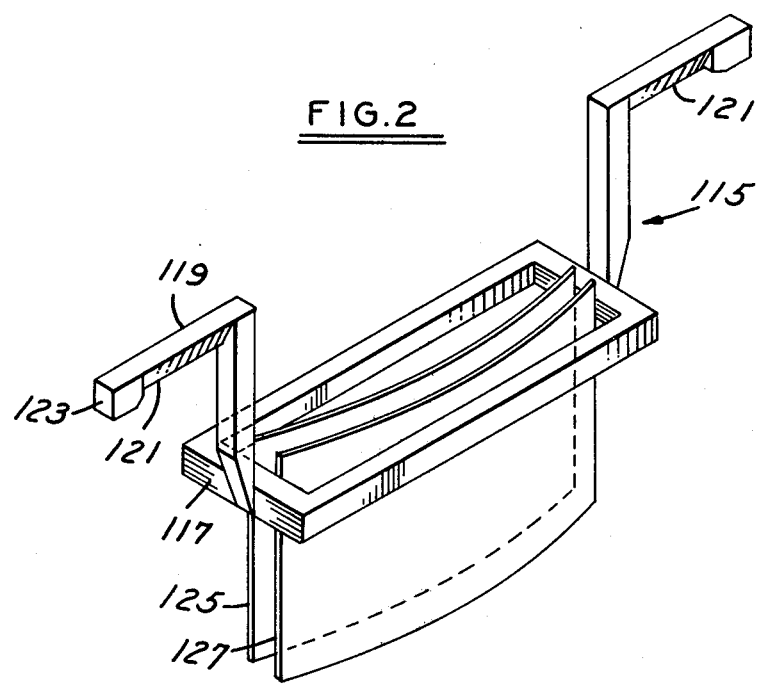
FIG. 2, is a perspective view of the plate holder rack, on an increased scale and illustrating the mounting of a pair of upright electropheric plates.

There is employed the plate holder 115 FIG. 2, which includes an elongated horizontally disposed rectangular frame 117 and at its opposite ends a pair of outwardly directed inverted L-shaped support arms 119 terminating in stops 123. Undersurface portions 121 of the arms 119 are of V-shape adapted for cooperative supporting registry within the corresponding V-shaped notches 29 along the upper edges of the housing front and rear walls. One or a series of parallel spaced rectangular sample plates 125 are arranged in an upright position, bowed or flexed as shown and are, nested lengthwise within the frame 117 of the plate holder rack 115 and are frictionally retained therein, FIG. 2.

Each of the sample plates 125 are electrically nonconductive such as of a plastic material having a MYLAR (Trademark) backing for illustration, and upon the opposite side an electrophoresis media, such as cellulose acetate. The electrophoresis media may be of other materials (agarose, cellulose esters, acrylamide gel, etc.) which are known to be electrically conductive for use in the electrophoresis method, such as disclosed in the U.S. Pat. No. 3,808,118 of April 30, 1974 and issued to Applicant's Assignee, Helena Laboratories Corporation, Beaumount, Texas.

Each of the opposed parallel spaced lift and transfer plates 81 are positioned within the cabinet 13 and outwardly of the housing front and rear walls 19 and 21. The lift and transfer plates 81 terminate at their upper ends in the elongated top plates 129 which have at their inner edges the upright flanges 131 along which are provided opposed pairs of longitudinally spaced V-notches 133, FIGS. 1, 3 and 8.

A pair of cover stops 135 are mounted upon top plates 129 and are positioned under the electrophoresis chamber cover 39 when this cover is in the closed position shown in FIG. 1. A pair of spaced yieldable cover spring latches 137 are anchored at 139 upon the top plates 129 and are adapted to retain the cover 39 when in the closed position shown in FIG. 1 in registry with cover stops 135, closing off the electrophoresis chamber 37, FIGS. 1 and 9.

POWER OPERATED LIFT AND TRANSFER ASSEMBLY

The respective parallel spaced lift plates 81, FIGS. 3–8 interconnected by the connector rods 141 and the plate connector 83 at one end, function as a walking beam and are adapted to progressively lift, transfer and lower the plate holder 115 with the vertically mounted plates 125 from chamber 37 and progressively into each of the opposed pairs of notches 29 in the housing front and rear walls and with respect to the underlying vats 45, 47, 49, 51, 53, 55 and drying chamber 57.

The rack 115, FIG. 2, at all times maintains the plates 125 in an upright position so that after the electrophoresis process, the plates are lifted in a vertical plane, by the lift and transfer assembly and moved forwardly and downwardly to the next succeeding opposed pair of housing support notches 29 such as for immersion within the stain fluid within vat 45, FIG. 9.

After the electrophoresis process, upon the initial activation of the power operated lift and transfer assembly, upward movement of the lift plates 81 release the latches 137 from the chamber cover 39 and the stops 135 automatically swing the cover 39 from the position shown in FIG. 1, until it moves into the position shown in FIG. 3.

The succession of movements of the lift plates 81, as schematically illustrated in FIGS. 4, 5, 6 and 7, define a linear stepping motion by which the loaded plate rack 115 is transported from the electrophoresis chamber 37 with the plates lowered into the fluid within the stain vat 45 for immersion therein for a predetermined interval. On successive lift and transfer movements of the lift and transfer assembly, the stained plates are successively lifted, advanced and lowered into the respective solutions within the additional vats successively, namely vats 47, 49, 51, 53 and 55 and ultimately into the drying chamber 57.

The power mechanism for operating the lift and transfer assembly or lift plates 81 includes the electric motor 143, FIG. 8, which is mounted and supported at 144 upon the undersurface of housing platform 25 and has an output shaft which projects through wall 19 and mounts drive sprocket 145, also shown in FIG. 4. The sprocket 145 which is in driving engagement with drive chain 147, is supported at its opposite ends upon the laterally spaced transfer sprockets 149, FIG. 8.

These transfer sprockets are mounted upon transverse axle shafts 151, which are journalled through the bushings 153 through the front and rear walls 19 and 21 of the housing 17, projecting outwardly thereof. Outwardly of the housing front and rear walls, the opposed longitudinally spaced pairs of lift chain drive sprockets 155 are secured upon the outer ends of the axle shafts 151, FIG. 8 for rotation therewith.

Opposed longitudinally spaced pairs of lift chain sprockets 155 are spaced above the first mentioned lift chain sprockets 155 and journalled upon the respective outwardly extending stud shafts 157. The respective opposed pairs of longitudinally spaced lift chains 159 are arranged outwardly of the housing front and rear walls 19 and 21 and are mounted over the corresponding lift chain sprockets 155 as shown in FIGS. 4, 5, 6, 7 and 8.

Projecting outwardly from the respective lift chains 159 are the lift pins 161 which are outward of the housing front and rear walls, which extend into bushings 162 arranged towards the bottom of the respective lift plates 81 adjacent their respective ends. Since the lift chains 158 move in unison when the motor 143 is energized, the corresponding interconnected lift plates 81 move in unison through the four positions thereof shown respectively in FIGS. 4, 5, 6 and 7.

When the lift plates 81 are in their substantially lowermost positions, such as shown in FIGS. 4 and 7, the top edges thereof are positioned so as to be slightly below the top wall 163 of cabinet 13. Respective lift plates 81 have formed therethrough a series of rows of longitudinally spaced apertures 191 for reducing their weight and accordingly the load placed upon motor 143 as illustrated in FIG. 3.

CONTROL PANEL

On the upper portion of the cabinet 13, the front thereof, has the elongated inclined control panel 15, FIG. 1, which has at one end the basic off and on power switch 167 connected to the suitable source of electrical power. Within the cabinet adjacent the control panel is a timer, having a timer control knob 169, which can be preset for the electrophoresis process from between 0 to 60 minutes as shown in a control panel. The average time under certain conditions being 5-30 minutes, for illustration. The time of the electrophoresis process will be predetermined taking into consideration the nature of the serum or other sample specimens, which has been applied to the buffer moistened electrophoresis plates 125.

A manally operable voltage control switch is shown at 171, upon the control panel 15 by which, for a particular electrophoresis process, the voltage may be selectively set at 180, 300 or 350 volts, for illustration. A light emitting diode (LED) or indicator light is shown at 173 directly above the voltage switch 171 to indicate that the timer 169 is active and electrical power is being delivered to the electrophoresis chamber 37.

The control panel 15 also includes thereon, the stain cycle program switch 175 which shows eight different positions for preselection of one of eight different programs covering the preselected time of immersion of the plates after the electrophoresis process, within the respective solutions including the stain solutions in vat 45 and successively, the other process or treating solutions within the additional vats 47, 49, 51, 53, and 55 as well as the drying chamber 57. The average time of immersion for program 1 for illustration is 5 minutes within each of the respective vats 45 through 55 and the drying chamber 57. The program switch 175 also has a manual position indicated on the control panel 15 for manual operation. Here the immersion time within the respective vats can be manually controlled, one at a time. The cycle start button is shown at 177 and a stop button at 179 is located upon the control panel 15 for initiating or stopping the basic automatic operation of the electrophoresis staining apparatus 11.

MANUAL OPERATION

In the event that manual operation is desired and the program knob 175 has been turned to the "manual position", there is employed a step switch 181 upon the control panel 15 which will control the movements of the lift and transfer assembly 81 intermittently from the staining vat 45 successively through the respective vats 47, 49, 51, 53, 55 and the drying chamber 57 on intermittent activation of the step switch 181.

In normal operation with automatic functioning of the present apparatus, the heater 71 and the blower 67, FIG. 10, are automatically activated. Under manual operation, with the program switch 175 so set, the toggle switch 183 for the heater 71 and toggle switch 185 for the blower 67 must be manually moved to the "on" position.

Mounted upon the rear top wall 163 of the cabinets, FIG. 8, is a plus-minus polarity switch 187 and a pair of spaced fuse holders 189. These are interposed into the electrical circuit directing power into the electrophoretic circuit within the electrophoresis chamber 37 and including the tilt switches 105 and 107, FIG. 9.

METHOD OF ELECTROPHORESIS

The invention is further directed to the method of electrophoresis which includes the following steps:

1. Supporting in an upright position, a non-conductive plate 125 having on one surface an electrophoresis media 127 to which has been applied a sample selected from the group consisting of serum proteins, lipoproteins, hemoglobins and isoenzymes for example. The supporting of the plate 125 or a plurality of such plates 125, employs a plate holder rack at 115, FIG. 2, which includes the horizontally open frame 117 within which the plates 125 are bowed and frictionally retained in the upright position shown. The plates 125 are supported upon the housing 17 for suspension within the electrophoresis chamber 37, FIG. 9.

2. A further step, includes the enclosing of the plate or plates 125 within the chamber 37 by closing the cover 39, FIG. 9 and thereafter applying an electrical potential to the plate ends within an electrical power circuit for a preselected period at a preselected voltage, wherein the specimen ingredients fractionate and migrate laterally through portions of the electrophoresis media 127.

In the illustrative embodiment, the electrophoresis media is a cellulose acetate, but it could be made of other electrophoresis media, such as agarose, cellulose esters, acrylamide gel and other types for plate electrophoresis.

In the present method, the electrophoresis chamber 37 has a hinged cover 39 wherein the application of electrical potential includes the spaced electrical conductors 87 and 101 on the bottom of the container 33 and within the cover mounted upper sponge support 99 respectively.

3. The method includes the positioning of a buffer moistened conductive sponge 95 within a buffer solution 93, within the container to overlie the conductor 87 and thereafter the positioning of a second buffer moistened conductive sponge 111 within the sponge holder 99 depending from the cover 39 in engagement with the second conductor 101. The method includes the positioning of the top and bottom edges of the plates 125 so as to be yieldably embedded into the surfaces of the respective sponges for completing the electrical circuit therethrough when the cover 39 is in the closed position shown in FIG. 9 with the normally opened tilt switches 105 and 107 closed.

The present method includes the use of a plate supporting and transfer rack 115 having an open framework 117, with the plates 125 being horizontally bowed for frictional retention therein.

4. The present method includes the further step of elevating the plate or plates 125 after the electrophoresis process and translating the plates while maintaining them in an upright position and thereafter lowering the plates and immersing them within a stain solution for a predetermined interval.

5. The present method also includes in connection with the use of a power operated lift and transfer assembly 81, a means by which the plate holder rack 115 and the mounted plates 125-127 are successively transferred and immersed within their respective solutions in the vats 45, 47, 49, 51, 53 and 55 and within the drying chamber 57, for a predetermined period in a continuous linear stepping motion.

OPERATION

For illustration, the cabinet 13 of the vertical electrophoresis and staining instrument, or apparatus 11, is 21 inches wide, 13 inches deep and 7 inches tall. The apparatus 11 is unique in that the same plates 125 are handled vertically rather than horizontally for the electrophoresis. The samples are also handled vertically for staining as well as for treatment within the respective solutions for rinsing, fixing and drying the plates 125. Since all of the samples are held in the same way, automating the present electrophoresis staining process is facilitated.

For the electrophoresis process, the technician pours a small amount of buffer solution 93, FIG. 9, into the bottom 85 of chamber 33, being careful not to cover the sponge 95. He then places the sample holder 115 with the sample plates 125 into the chamber 37. He fits the two arms 119 thereof, FIG. 2, with their V-shaped undersurfaces 121 in registry with the V-notches 29 on the housing front and rear walls. The plates 125 will push gently into the sponge 95 and will thus come into contact with the buffer solution therein. Lid or cover 39 of the chamber 37, has mounted thereon a pair of tilt switches 105 and 107, one of the switches controlling the flow of electrical current to the platinum wire electrode 87. An additional electrode 101 is placed within the sponge holder 99 and an additional sponge 111 nested up into the holder and held thereon by a pair of rubber bands 113. When the lid 39 is in the down position shown in FIG. 9, its depending contact 109 is in registry with the top contact 91 at the top of the chamber 37, which is electrically connected to conductor 87.

The tilt switches 109, 107 close only when the cover 39 is in the down position and open when the cover has been elevated, protect the user from accidental shock. The top sponge 111 is likewise dampened with the buffer solution. The sample plates 125 will push into the top sponge when the cover 39 is closed, thus making electrical contact with both ends of the plates to complete the electrophoretic circuit.

STAIN AND WASH VATS

These six vats, preferably of plastic, are aligned with the electrophoresis chamber 37 upon the housing platform 25 so that the plates 125 can be immersed into each thereof in their proper order, i.e., dye for vat 45, rinse solution number 1 for vat 47, rinse solution number 2 for vat 49, rinse solution number 3 for vat 51, a fixative solution for vat 53 and a rinse for vat 55. Each vat is removable for cleaning, facilitated by the apertured upper tabs 59 on each vat.

DRYING CHAMBER

This metal chamber 57, FIG. 10 is at the end of the vats and is approximately the same size thereof and has an opening 77 toward the bottom thereof to allow warm air to enter from the warm air passages 69 and 75 for drying the plates as shown by the arrows and of movement of air upwardly.

The fan 67 forces air past the cylindrical heating element 71 which moves through the metal grate 73 and passage 75. The air is deflected by the cross plate 83, which connects the right hand ends of the respective lift plates 81, deflecting air into the base of drying chamber 57. The air circulates, rises and dries the sample plates.

TRANSFER PROCESS

The transfer mechanism includes a network of chains 147 and 159 with associated sprockets driven by motor 143 for moving the horizontal drive chain 147 mounted upon the corresponding transfer sprockets 149. These sprockets are in driving engagement with the transverse longitudinally spaced axle shafts 151. The respective power rotative shafts activate the lowermost drive sprockets 155 for the lift chains 159 whose upper ends are journalled over the idler sprockets 155 arranged upon opposite sides of the housing FIGS. 4, 5, 6, 7 and 8.

As the drive chain turns the transfer sprockets 155 and their axles 151, the lower chain sprockets 155 also turn. Each of the lift chains 159 has an outwardly directed lift pin 161 which is supportedly journalled within corresponding bushing 162 within the lift plates 81 adjacent their opposite lower ends.

The lift plates 81 produce a linear stepping motion for the sample holder rack 115 mounting the sample plate or a plurality of upright sample plates as they move. The plates 125 rise as the arms 119 of the sample holder 115 nest in the opposed notches 133 in the lift plates 81. This lifts the sample plates entirely out of the respective chamber. The sample is then carried forward and the rack is lowered into the housing notches 29, which center it with respect to the next adjacent vat, such as the staining vat 45 and the successive vats 47, 49, 51, 53, 55 and drying chamber 57.

In connection with the electrophoresis chamber 37, lift plates 81 on upward movement engage the lid or cover 39 and lift it up and back. This "flipping back" of the lid insures that the upper sponge holder 99 is moved well out of the path of travel of the sample holder 115 as it is lifted from the chamber 37.

CONTROL PANEL

The power switch 167 turns the apparatus 11 on and off.

ELECTROPHORESIS SECTION

Time control 169 determines the length of time that the voltage is applied to the electrophoresis process within chamber 37. Time is variable between 0 and 60 minutes. Voltage switch 171 determines the amount of voltage to be applied to the sample plates during electrophoresis, as an example, 180, 300 or 350 volts. Voltage LED (light emitting diode) 173 lights up when the timer is active and the current is flowing through the electrodes 87 and 101.

A range switch alters the range of an ammeter, which is located directly above the range switch. In the normal position, the ammeter readings are taken at face value. In the "X2 position", doubles the face value, increasing the range meter to 40 MA.

STAIN CYCLE SECTION

PROGRAM SWITCH

The nine position rotary program switch 175 selects the internal program which will control the length of time that the samples are left in each of the staining cycle chambers 45 through 55. "Manual" position allows the user to control the time that the samples spend in each chamber. The start button 177 allows a selected program to begin. The stop push button 179 stops the selected program.

MANUAL OPERATION CONTROLS

The step button 181 and the heater and blower switches 183 and 185 are provided to allow the user manual operation of cycles not programmed into the apparatus 11.

The step button 181 activates the transfer process for one position at a time and arranged above the respective buttons, are a series of registering indicators LEDS 173 which illuminate when the corresponding button is pushed. The heater toggle switch 183 turns on the heating element 71 beneath the drying chamber 57. The blower toggle switch 185 activates the fan 67 which forces air to pass over heating element 71 and into the drying chamber 57.

With respect to the electrophoresis chamber 37, the sponges 95 and 111 act as electrophoresis wicks. Both of the sponges should be clean and free of contamination or stains. Each of the sponge wicks should be soaked in fresh cold buffer, that has been mixed for a particular procedure. After completely wetting the sponge wicks in a buffer, these are removed and the excess buffer squeezed out. The wicks should be wet, but not dripping. Excess buffer in the sponge wicks 95, 111 may cause distortion of the electrophoretic pattern or an irregular migration time. A dry sponge may cause poor electrophoretic contact, excessive production of heat, both of which adversely affect results. After applying the samples to be tested to the electrophoresis plate 125, the respective plate is mounted within the carrying rack 115, such as shown in FIG. 2 with the respective plates 125 bowed as shown and frictionally retained in position.

In the illustrative embodiment, the sample plates 125-127 are arranged within the rack 115, FIG. 2, with the respective electrophoresis plates facing in the same direction wherein the top of the cellulose acetate plate is approximately 5 MM (one quarter inch) above the bottom of the sample carrying rack 115. Thereafter, the carrying rack 115 with the depending upright plates, with the samples applied, are initially mounted so that the respective rack arms 119 rest within the corresponding notches 29 in the housing on opposite sides thereof, as shown in FIG. 9 for the beginning of the electrophoresis process. The arms 119 are also normally slightly spaced above the corresponding aligned notches 133 of the lift and transfer plates 81.

The lid 39 is tilted over until it locks in place relative to the latches 137. The polarity switch 187, FIG. 8 is checked for the proper polarity. The electrophoresis pattern will migrate from the negative (cathodic) to the positive (anode) pole. The negative setting will electrophoresis the samples downward. A positive setting will electrophoresis the sample upward. Preliminary testing of the present system indicates that a negative setting and downward electrophoretic migration is preferred. Under certain other conditions a positive setting or polarity may be preferred.

After the chamber lid 39 is locked in place, the power switch 167 is turned to the on position, FIG. 1. It takes approximately 1 minute for the unit to warm up. The electrophoresis plates are subject to some dehydration during the application process, particularly if more than one plate is being used. This one minute delay also allows the plates in the chamber to rehydrate with buffer solution. Thereafter, the voltage switch 171 is moved to the desired setting of either 350, 300 or 180 volts.

The knob 175 is set to one program as for example, program number 1. This program initiates a five minute staining cycle for each of the compartments or vats other than the electrophoresis chamber. Other programs are contemplated by which time of immersion in the respective vats involving the various solutions can be varied as desired and preset depending upon the programs selected. Both the heater and blower switches 183 and 185 should be in the down position. The heater 71 and blower 67 will automatically turn on near the end of the clearing solution cycle. In order to override the staining cycle, as determined by program number 1, the staining cycle control knob can be turned to the manual position shown at 175. The manual mode allows the operator to initiate the desired steps by pressing the step button 181. The heater 71 and blower 67 may also be activated in the manual mode by placing the toggle switches 183 and 185 in the on position.

In the illustrative embodiment, the end of the electrophoresis preset time will be signalled by a bell. After a three second delay, the lid 39 of the chamber 37, will be automatically lifted to an inoperative position and the staining cycle will begin. The rack 115 and plates suspended in a vertical position, will be automatically transferred through the various solutions ending with a five minute cycle in the drying compartment 57.

The plates are then ready for visual inspection or densitometry.

STAINING COMPARTMENTS

In the illustrative embodiment, a stain referred to as "PONCEAU S" is employed within the stain vat 45 in a solution which is filled into the vat 45 to within 10 MM of the top to assure complete staining of the electrophoresis media 127.

The first rinsing compartment 47 for example, contains a solution of 5% GLACIAL acetatic acid. The second rinsing compartment 49 also contains a 5% GLACIAL acetatic acid. The third rinsing compartment also contains the 5% GLACIAL acetatic acid.

The fixing vat or compartment 53 contains a methanol solution. The methanol dehydrates the plate or plates 125 and removes the excessive water. The methanol should be changed daily or after dehydrating 10 plates. A contaminated methanol will create a cloudy background on the finished plate.

The clearing compartment vat 55 contains a clearing solution which is composed of:
  67 parts Methanol
  28 parts Glacial Acetatic Acid
  4 parts Clear Aid (Helena Catalogue No. 5005)
The clearing solution should be changed regularly to insure proper clearing of the cellulose acetate. The clearing solution is used to soften the cellulose acetate media or other media employed. The actual clearing of the cellulose acetate takes place during the drying cycle within chamber 57.

Within the drying chamber, the plates 125 are normally dried for 5 minutes. If extra drying time is desired, the switch for the dryer at 183 and 185 is turned on. The plate should be dried until the acetate surface is hard and dry. Excessive drying of the cellulose acetate plate or other media on the plate, may create delamination of the media from the plastic backing plate.

LIPOPROTEIN ELECTROPHORESIS

The electrophoresis is employed in the chamber 37 using the same technique as would be employed for serum protein. To stain the lipoprotein plate, the operator must substitute for the Ponceau S in the chamber 45 with one filled with oil red Om and 1.0 normal sodium hydroxide.
  330 mL Oil Red Om
  110 mL 1.0 Normal Sodium Hydroxide
The program switch 175 should be set for manual so that the lipoprotein plate can stain for a recommended time of 1 hour approximately.

HEMOGLOBIN ELECTROPHORESIS

This requires an offset application. Migration will be from the negative to the positive. Thus, the polarity switch should be switched to positive. Staining, destaining and clearing of hemoglobins is identical to the serum protein format, using program 1.

With respect to the voltage control knob 171, lipoproteins should be run at 180 volts for 25 minutes. The hemoglobins should be preformed at 350 volts for 25 minutes.

Having described my invention, reference should now be had to the following claims:

I claim:

1. An automated electrophoresis and staining apparatus comprising a cabinet having an apertured top wall;
   an elongated housing spaced within said cabinet having upright front and rear walls, an end wall, a bottom wall and a platform between said front and rear walls overlying said bottom wall with said front and rear walls projecting above said top wall;
   an electrophoresis chamber adapted to contain a buffer solution mounted upon said platform at one end of said housing;
   and a series of vats mounted upon said platform arranged in a row and aligned with said chamber, adapted to contain respectively a liquid stain and a series of processing solutions;
   said front and rear walls having transversely aligned longitudinally spaced pairs of notches in and along their upper edges;
   said pairs of notches being over and in alignment with the centerline of each of said vats and chamber respectively;
   a plate holder rack overlying said electrophoresis chamber including a horizontal frame and at its ends a pair of outwardly projecting inverted L-shaped arms respectively nested in the pair of notches in registry with said chamber;
   and adapted for supporting one or a plurality of upright electrophoresis plates onto which has been applied a sample for electrophoretic fractionization;
   said plates selected from the group consisting of cellulose acetate, cellulose esters, agarose, acrylamide gel and any other media suitable for electrophoresis;
   said plate or plates being nested within said chamber within an electrophoretic circuit between a cathode and anode for a predetermined period;
   and a power operated lift and transfer assembly within said cabinet outwardly of said front and rear walls adapted to progressively lift, transfer and lower said plate holder and plates from said chamber and progressively into each of said pairs of notches and underlying vats for a predetermined period successively in a linear stepping motion;
   whereby said plates in an upright position are immersed into the fluids within said vats.

2. In the electrophoresis apparatus of claim 1, there being an upright plate drying chamber within said housing, above said platform, between the last of said vats and the housing end wall;
   and power means within said housing, below said platform for supplying heated air to the base of said drying chamber for upward movement therethrough;
   there being an additional pair of housing wall notches in registry with said drying chamber;
   said transfer assembly adapted to position and support said rack within said latter notches for suspension thereof within said drying chamber.

3. In the electrophoresis apparatus of claim 1, said electrophoresis chamber including a cover pivoted upon said housing, spanning its front and rear walls, overlying said lift and transfer assembly and closing said chamber.

4. In the electrophoresis apparatus of claim 3, an elongated sponge holder underlying said cover adapted to support an elongated buffer moistened sponge;
   there being an elongated buffer moistened sponge within the bottom of said chamber;
   said electrophoretic circuit including electrodes connected to a power source and in engagement with said sponges respectively, said sample mounted plates at their tops and bottoms being in engagement with said sponges for completing the circuit between said electrodes.

5. In the electrophoresis apparatus of claim 4, a pair of normally opened tilt switches mounted upon said cover and connected into said circuit, for closing said circuit only when the cover is in the horizontal position.

6. In the electrophoresis apparatus of claim 5, said circuit including a stationary contact within said chamber connected to one of said electrodes;
   and a movable contact on and depending from said cover connected to one of said tilt switches, for closing said circuit when said cover is in a horizontal position.

7. In the electrophoresis apparatus of claim 3, yieldable latches upon said lift and transfer assembly anchoring said cover in closed position when said assembly is in its lowermost retracted position, upward movement of said lift and transfer assembly, tilting said cover upwardly and out of the path of upward movement of said plate carrying rack.

8. In the electrophoresis apparatus of claim 1, said chamber and each of said vats at their upper ends having an upright lift tab to facilitate loading and unloading thereof into and from said housing.

9. In the electrophoresis apparatus of claim 1, portions of said rack arms along their undersurfaces being shaped for cooperative registry with said pairs of housing notches.

10. In the electrophoresis apparatus of claim 1, said electrophoresis plates being flexed for upright frictional retention within said rack frame.

11. In the electrophoresis apparatus of claim 1, said lift and transfer assembly being a walking beam device including a pair of upright parallel interconnected lift and transfer plates, outward of the housing front and rear walls, and movably mounted thereon, said plates adapted for successive movements upwardly, forwardly, downwardly and rearwardly;
    said upward movement lifting said plate holder rack from one pair of housing notches, said forward movement transferring said rack to overlie the next adjacent pair of housing notches;
    said downward movement positioning said rack upon said latter pair of notches, further downward movement disengaging said lift plates from said rack, and said rearward movement repositioning said lift plates to their initial position.

12. In the electrophoresis apparatus of claim 11, said lift and transfer plates having transversely aligned longitudinally spaced pairs of notches in and along their upper edges;
said pairs of notches being in alignment with the corresponding housing pairs of notches respectively;
said rack arms overlying said lift and transfer plates adapted for nesting and support within the lift and transfer plate notches upon upward movement of said lift and transfer plates;
whereby the respective pairs of notches in said lift and transfer plates successively receive said rack arms as they are progressively transferred to successive pairs of housing notches until the rack and its vertically supported plates have been transferred successively from the electrophoresis chamber, and into each of the respective vats for predetermined intervals.

13. In the electrophoresis apparatus of claim 12, the housing and lift plate notches being V shaped;
portions of said rack arms along their undersurfaces being V-shaped for cooperative registry with said pairs of housing and lift plate notches.

14. In the electrophoresis apparatus of claim 11, the mounting of said lift and transfer plates upon said housing including transversely opposed pairs of longitudinally spaced lift sprocket chains journalled upon and outwardly of said housing adjacent its opposite ends and movable in unison;
and corresponding outwardly directed lift pins upon each sprocket chain extending through and journalled within said lift and transfer plates adjacent their lower ends respectively.

15. In the electrophoresis apparatus of claim 14, the supporting of said sprocket chains including idler sprocket gears journalled upon said housing receiving the upper end of each sprocket chain respectively;
drive sprocket gears rotatably journalled upon said housing operatively receiving the lower end of each sprocket chain respectively;
and power means upon said housing operatively engaging said drive sprocket gears.

16. In the electrophoresis apparatus of claim 15, said power means including a motor mounted upon said housing having a drive shaft mounting a sprocket gear;
a pair of longitudinally spaced transverse axle shafts journalled upon said housing and projecting from opposite sides thereof;
said shafts mounting at their ends the respective drive sprocket gears for said lift sprocket chains;
transfer sprocket gears secured upon each axle shaft;
and a drive chain interconnecting said transfer sprocket gears and operatively engaged by said motor shaft sprocket gear.

17. In the electrophoresis apparatus of claim 16, the pin connection between said lift sprocket chains and said lift plates being such that said lift and transfer plates move in unison upwardly, forwardly, downwardly and rearwardly;
and an electrical circuit including said motor connected to a power source, and including a pre-set adjustable program timer interrupting movements of said lift and transfer plates for predetermined intervals.

18. In the electrophoresis apparatus of claim 2, said power means including a fan, an air conduit aligned therewith having an outlet communicating with the base of said drying chamber;
and an electric resistance heater in said conduit.

19. In the electrophoresis apparatus of claim 3, a transverse stop on said cabinet limiting opening movement of said cover;
at a stop upon said lift and transfer assembly engageable with said cover when closed, and adapted for opening said cover on upward movement of said lift and transfer assembly.

20. In the electrophoresis apparatus of claim 1, said electrophoretic circuit including a power source and a voltage switch for selectively producing 180, 300, 350 volts to said circuit;
depending upon the nature of the sample, and a + − polarity switch in said circuit for preselecting polarity between said anode and cathode for upward and downward migration respectively.

21. In the electrophoresis apparatus of claim 11, said lift plates having formed therethrough a series of rows of longitudinally spaced weight reducing cut-outs therein.

22. In the electrophoresis apparatus of claim 11, there being an upright plate drying chamber within said housing, upon said platform between the last vat and the housing end wall;
the connection between said lift plates including an end plate extending between the one ends of said lift plates at their lower ends adapted for registry with said plate drying chamber.

23. In the electrophoresis apparatus of claim 11, the top of said lift plates when in their lowermost position being substantially enclosed within said cabinet.

24. In the electrophoresis apparatus of claim 1, said circuit including an electrical power source, a motor for driving said lift and transfer assembly, a timer for presetting the length of time that the voltage is applied to said electrophoresis chamber;
a control panel on said cabinet having an off and on switch connected into said circuit, a voltage selector connected into said circuit for variably selecting 180, 300 and 350 volts delivered to the electrophoresis chamber; and
a time control connected to said timer and variable between 0 and 60 minutes, and a multiple position program switch for presetting the length of time the sample plates are left in each of the stain cycle vats, or for manual control thereof.

25. The method of electrophoresis and staining which includes:
supporting in an upright position a non-conductive plate having on one surface an electrophoresis media to which has been applied a sample selected from the group consisting of serum proteins, lipoproteins, hemoglobins and isoenzymes;
enclosing said plate within a chamber;
applying an electrical potential to the plate ends within an electrical power circuit for a preselected period, and at a preselected voltage the specimen fractionating and migrating laterally over portions of said plate;
elevating said plate after electrophoresis;
laterally translating said plate while maintaining it in an upright position;
and lowering said plate immersing it within a staining solution for a predetermined interval.

26. In the method of claim 25, said electrophoresis media selected from the group consisting of cellulose acetate, agarose, cellulose esters, acrylamide gel and any other media suitable for electrophoresis.

27. In the method of claim 25, said chamber having a hinged cover, said application of the electrical potential including electric conductors on the bottom of said chamber and in said cover respectively;

and positioning a buffer moistened conductive sponge within a buffer solution within said container to overlie one conductor and a second buffer moistened conductive sponge within said cover engaging the other conductor, the top and bottom edges of said plate being yieldably embedded into the surfaces of said sponges respectively for completing the electrical circuit therethrough.

28. In the method of claim 25, the supporting of said plate including a rack having a horizontal open frame; said plate being bowed horizontally for frictional retention within said rack in an upright position.

29. In the electrophoresis apparatus of claim 1, said series of processing solutions including treating solutions 1, 2 and 3, a fixative solution and a rinse solution.

30. In the electrophoresis apparatus of claim 9, said notches being V-shaped, said rack undersurfaces being V-shaped.

* * * * *